United States Patent
Scheiner et al.

(10) Patent No.: US 7,142,920 B2
(45) Date of Patent: Nov. 28, 2006

(54) CHRONOTROPIC STATUS MONITOR FOR IMPLANTABLE CARDIAC DEVICE

(75) Inventors: Avram Scheiner, Vadnais Heights, MN (US); Donald Hopper, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 174 days.

(21) Appl. No.: 10/853,574

(22) Filed: May 25, 2004

(65) Prior Publication Data

US 2005/0267541 A1    Dec. 1, 2005

(51) Int. Cl.
*A61N 1/30*    (2006.01)
(52) U.S. Cl. .................................................. 607/17
(58) Field of Classification Search ............ 607/17–27; 600/483, 484
See application file for complete search history.

(56) References Cited

U.S. PATENT DOCUMENTS

| 5,476,483 | A   | 12/1995 | Bornzin et al. |
| 5,514,162 | A   | 5/1996  | Bornzin et al. |
| 6,129,744 | A   | 10/2000 | Boute |
| 6,161,042 | A   | 12/2000 | Hartley et al. |
| 6,190,324 | B1  | 2/2001  | Kieval et al. |
| 6,277,078 | B1  | 8/2001  | Porat et al. |
| 6,304,774 | B1  | 10/2001 | Gorman |
| 6,408,208 | B1  | 6/2002  | Sun |
| 6,456,880 | B1* | 9/2002  | Park et al. ................... 607/25 |
| 6,490,485 | B1  | 12/2002 | Sun et al. |
| 6,572,557 | B1* | 6/2003  | Tchou et al. ................ 600/483 |
| 6,795,734 | B1* | 9/2004  | Vanderlinde et al. ......... 607/27 |

* cited by examiner

*Primary Examiner*—George Manuel
(74) *Attorney, Agent, or Firm*—Schwegman, Lundberg, Woessner, & Kluth, P.A.

(57) ABSTRACT

An implantable cardiac device with an exertion level sensor is programmed to determine a heart rate appropriate for a given measured exertion level in accordance with a physiological model and/or previously collected physiologic data. The device then compares the model's heart rate with a measured intrinsic heart rate. Based upon this data, the device is able to recognize changes in the patient's heart rate response and predict or recognize a chronotropically incompetent condition.

16 Claims, 2 Drawing Sheets

CHRONOTROPIC STATUS MONITOR FOR IMPLANTABLE CARDIAC DEVICE

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

In pacemaker patients who are chronotropically incompetent (e.g., sinus node dysfunction), the heart rate is determined solely by the pacemaker in the absence of intrinsic cardiac activity. That heart rate is determined by the programmed escape intervals of the pacemaker which cause paces to be delivered to the atria and/or ventricles, depending upon the pacing mode, if no intrinsic beats occur before expiration of the escape intervals. Pacing the heart at a fixed rate as determined by the length of the programmed escape intervals, however, does not allow the heart rate to increase with increased metabolic demand. It is for this reason that rate-adaptive pacemakers have been developed which vary the programmed escape intervals in accordance with one or more physiological parameters related to metabolic demand such as obtained from an accelerometer or minute ventilation sensor. In chronotropically competent patients in need of ventricular pacing, on the other hand, atrial triggered pacing modes such as DDD or VDD are desirable because they allow the pacing to track the physiologically normal atrial rhythm, which causes cardiac output to be responsive to the metabolic needs of the body. For this latter group of patients, the pacemaker is normally programmed so that the atrial rate is overridden by an atrial or ventricular pace only if the atrial rate drops to a level considered unsafe.

A change in a patient's chronotropic status from competent to incompetent after initial implantation of a cardiac rhythm management device is usually not addressed until the patient has become very symptomatic and has gone through a formal clinical evaluation via exercise testing. Only then is the patient provided with additional therapy such as reprogramming of the pacemaker to deliver rate-adaptive pacing. The present disclosure is directed toward ways of improving this situation.

DETAILED DESCRIPTION

Many patients implanted with a cardiac rhythm management device (e.g., a conventional pacemaker, resynchronization pacemaker, defibrillator, or combination device) have a normal heart rate (HR) response. That is, these patients are chronotropically competent so that the atrial rate as determined by the sino-atrial node responds appropriately to increased metabolic demand brought about by increased physical activity. The reason for which they are implanted with the device may be, for example, to restore of AV conduction, to treat ventricular conduction delays with resynchronization therapy, and/or to deliver anti-tachycardia pacing or defibrillation shocks in the event of an arrhythmia. After implantation, however, the condition of the patient often changes so that they are no longer chronotropically competent. As the condition progresses, the patient may eventually become severely symptomatic with fatigue and syncopal episodes. The present disclosure relates to an implantable cardiac device with an exertion level sensor which is programmed to determine a heart rate appropriate for a given measured exertion level in accordance with a physiological model and compare the model's heart rate with a measured intrinsic heart rate. Based upon this data, the device may be programmed to recognize changes in the patient's heart rate response before the patient becomes chronotropically incompetent. The device may also be programmed to send an alert message via a telemetry link that will alert a physician and the patient to changes in HR response, possibly before the patient becomes symptomatic. In another embodiment, where the device is a pacemaker programmed to deliver pacing in a non-rate-adaptive mode, the device may be programmed to automatically switch modes from non-sensor driven pacing (i.e., non-rate adaptive pacing) to a sensor driven (i.e., rate-adaptive) mode. The device may be further programmed to automatically set the correct sensor response based on previously monitored HR and sensor activity

1. Exemplary Implantable Device Description

Figure 1:
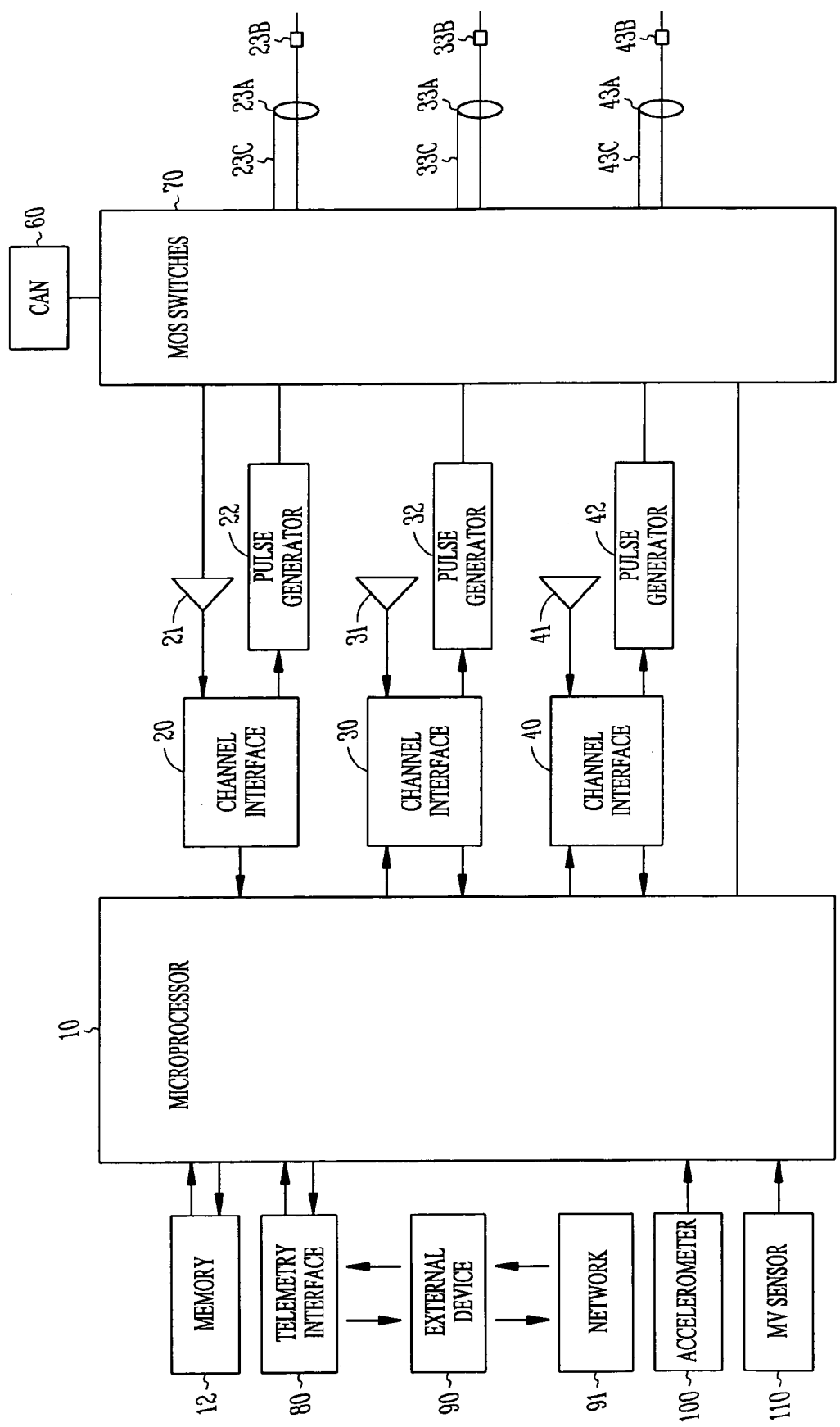
FIG. 1 is a block diagram of an exemplary cardiac rhythm management device for practicing the present invention.

Cardiac rhythm management devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. A block diagram of an exemplary implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external device 90 via a wireless telemetry link. The external device 90 may be an external programmer which can be used to program the implantable device as well as receive data from it or a remote monitoring unit. The external device 90 may also be interfaced to a patient management network 91 enabling the implantable device to transmit data and alarm messages to clinical personnel over the network. The network connection between the external device 90 and the patient management network 91 may be implemented by, for example, an internet connection, over a phone line, or via a cellular wireless link.

The embodiment shown in FIG. 1 has three sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. A sensing/pacing channel may include ring electrode 43a (33a or 23a) and tip electrode 43b (33b or 23b) of bipolar lead 43c (33c or 23c), sense amplifier 41 (31 or 21), pulse generator 42 (32 or 22), and a channel interface 40 (30 or 20). The channels may be configured as either atrial or ventricular channels. For example, the device may be configured for atrial pacing and either single ventricle or biventricular (resynchronization) pacing. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator (not shown) may also be interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates chamber sense signals (i.e., atrial or ventricular senses) when voltages sensed by the electrodes of a particular channel exceed a specified threshold. The controller 10 interprets sense signals from the sensing channels in order to detect arrhythmias and to control the delivery of paces in accordance with a pacing algorithm that employs such senses to trigger or inhibit pacing. Most pacing modes are so-called demand modes where a heart chamber is paced upon expiration of an escape interval without receipt of a sense from that chamber. For example, in an atrial triggered mode, an atrial sense initiates an AV escape interval so that one or both ventricles are then paced upon expiration of the interval if no intrinsic ventricular activity occurs beforehand. The ventricles may also be paced upon expiration of an escape interval initiated by a ventricular sense or pace, and the atria may be paced by a ventriculo-atrial escape interval initiated by a ventricular sense or pace.

Also interfaced to the controller are a minute ventilation sensor 110 and an accelerometer 100 for use in measuring a parameter related to the patient's exertion level and adjusting the pacing rate of the device accordingly in rate-adaptive pacing modes. The accelerometer and minute ventilation sensor produce a signal which approximates the patient's exertion level by measuring body activity and respiratory volume rate, respectively. The minute ventilation sensor measures the respiratory volume by injecting bursts of excitation current between excitation electrodes and measuring a transthoracic voltage drop to derive a signal proportional to the transthoracic impedance. (A particular minute ventilation sensor is described in U.S. Pat. No. 6,161,042, assigned to the assignee of the present application and hereby incorporated by reference in its entirety.) In a rate-adaptive pacing mode, one or more escape intervals are adjusted in accordance with a measured exertion level so that the pacing rate varies with metabolic demand. The modified pacing rate dictated by a rate-adaptive algorithm is referred to as the sensor-indicated rate. The rate-adaptive algorithm calculates the sensor-indicated rate by mapping a measured exertion level to a heart rate in accordance with a function referred to as the response factor.

2. Monitoring of Chronotropic Status

As aforesaid, a chronotropically competent patient with a normal heart rate response may nonetheless be implanted with a pacemaker for delivering conventional or resynchronization pacing. In these cases, it is preferable that the device be programmed to deliver the pacing in a non-rate-adaptive atrial-triggered mode so that the patient's normal physiological mechanisms will determine heart rate. These patients may become chronotropically incompetent over time, however, and the device may be programmed to recognize this change as it occurs and before severe symptoms arise. Based on the "Wilkoff model" or other appropriate physiological exercise model of chronotropic response, appropriate predictive heart rates can be determined for given levels of exertion in a particular patient. Heart rates appropriate for a plurality of exertion levels may be derived from the model, either by the device or by other means and then stored in the device as a table. The device may then be programmed to record over time a heart rate profile along with an exertion level profile determined from an exertion level sensor such as an accelerometer or minute ventilation sensor. By comparing the recorded heart rate profile with predictive heart rates from the model, the device is able to determine if and when a change in chronotropic status occurs.

In a particular example embodiment, predictive and actual heart rates are trended in line graph or histogram form. The baseline variability between the predictive model and actual heart rates is then determined over some period of time and considered as normal since the patient is assumed to be chronotropically competent at the time of implantation. Subsequently, actual heart rates are compared to predictive heart rates at periodic intervals in order to monitor for changes in chronotropic status. If the difference between actual and predictive heart rates is within the normal range of variability, then no change in chronotropic status has occurred and the device continues to monitor. If the difference between predictive and actual heart rates is outside the normal range of variability, then a change in chronotropic status may be assumed to have occurred. If the actual heart rates are below the predictive heart rates by a small amount, the device activates an alert to the physician to be aware of the possible change in patient status and continues to monitor. If the actual heart rates are below the predicted heart rates by a large amount, the device activates an alert to the physician to be aware of the possible change in patient status and also initiates rate-adaptive pacing. The rate-adaptive response factor can be calculated by the device from data previously collected while the patient's heart rate response was normal.

Figure 2:
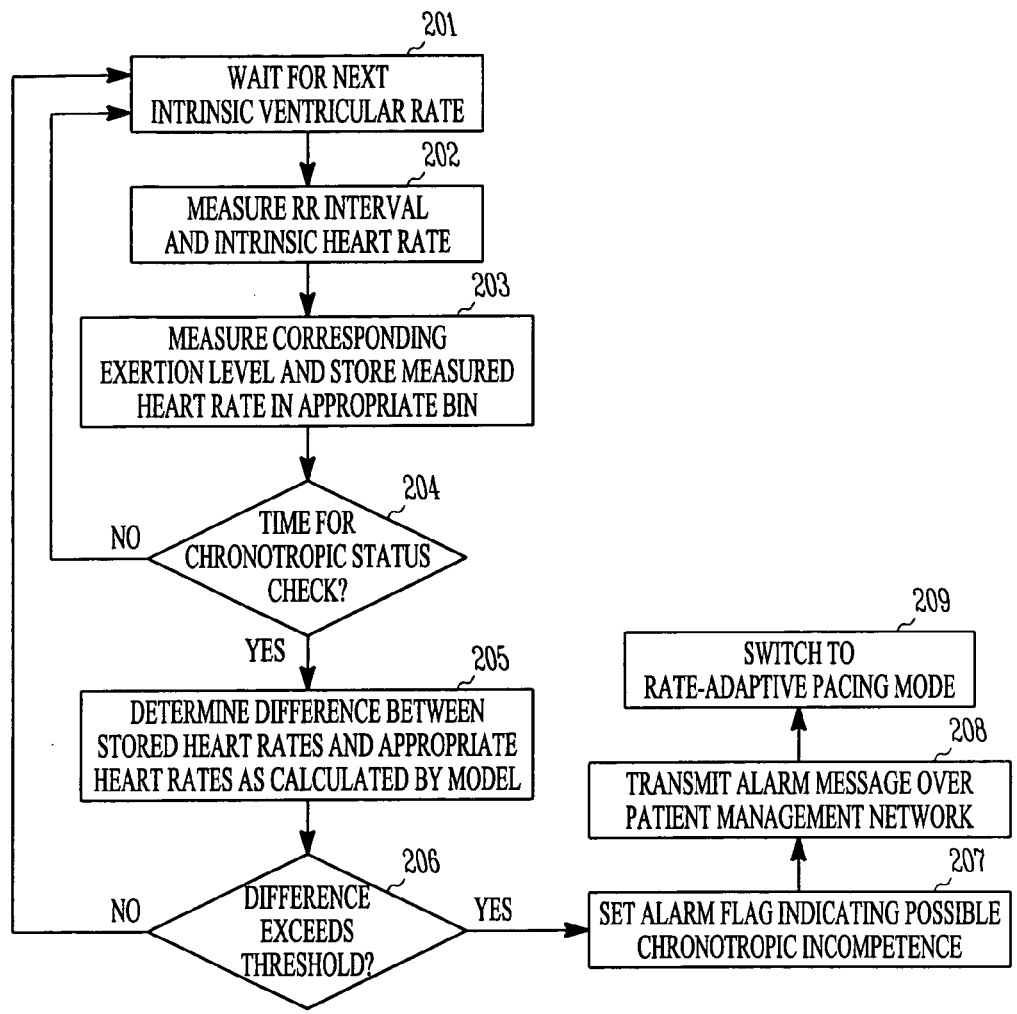
FIG. 2 illustrates an exemplary algorithm for monitoring chronotropic status.

Illustrated in FIG. 2 is an exemplary algorithm for monitoring chonotropic status by an implantable cardiac device as could be executed by an appropriately programmed device controller. The device, which may be a pacemaker, an implantable cardioverter/defibrillator, or cardiac monitoring device, is equipped with at least one sensing channel for generating intra-cardiac electrogram signals and an exertion level sensor interfaced to the controller for measuring a physiological parameter related to metabolic demand (e.g., an accelerometer or minute ventilation sensor). At step 201 the controller for detects intrinsic cardiac activity and, at step 202, measures the RR interval (i.e., the interval between ventricular beats) and an intrinsic heart rate from the electrogram signals. At step 203, the controller measures the corresponding exertion level and stores the measured heart rate in an appropriate bin, where each of a plurality of bins represents a particular exertion level. For each the exertion level bin, the stored heart rates may be averaged or otherwise statistically processed in order to eliminate normal heart rate variability. The controller may be programmed to record a patient's intrinsic heart rates along with corresponding measured exertion levels over some period of time before comparing the measured intrinsic heart rates with heart rates calculated as being appropriate for the measured exertion levels. At step 204, the device determines whether it is time to check the patient's chronotropic status. The device then determines the difference between the stored heart rates and the appropriate heart rates as calculated by the model at step 205. One way of determining the difference is to calculate a parameter reflecting the variability between a plurality of measured intrinsic heart rates and heart rates calculated by the model as being appropriate for the corresponding measured exertion levels. If the variability (or other difference metric) exceeds a predetermined threshold as determined at step 206, an alarm flag indicating possible chronotropic incompetence is set at step 207, where an alarm flag is any type of status indication which can be stored in memory. If the device is equipped with a telemetry interface for communicating with a remote monitoring device, the controller may be further programmed to send an alert message via the telemetry interface if the variability between measured intrinsic heart rates and calculated heart rates exceeds a predetermined value, shown in the figure as step 208. The alert message may be transmitted to a remote monitor and thence to clinical personnel via a patient management network. Finally, if the device is providing pacing therapy, the controller may be further programmed to switch to a rate-adaptive pacing mode if the variability between measured intrinsic heart rates and calculated heart rates exceeds a predetermined value, shown in the figure as step 209. The device may also calculate a response factor for rate-adaptive pacing based upon previously measured heart rates and exertion levels.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
   one or more sensing channels for generating intra-cardiac electrogram signals;
   a controller for detecting intrinsic cardiac activity and measuring an intrinsic heart rate from the electrogram signals;
   an exertion level sensor interfaced to the controller for measuring a physiological parameter related to metabolic demand; and,
   wherein the controller is programmed to:
   record a plurality of a patient's actual intrinsic heart rates along with corresponding measured exertion levels over a period of time;
   associate the actual heart rates with predicted heart rates for the corresponding measured exertion levels as calculated in accordance with a physiological model;
   calculate a parameter reflecting the variability between the actual heart rates and the predicted heart rates;
   compare the variability between the actual and predicted heart rates with a precomputed baseline variability; and,
   determine that a change in chronotropic status has occurred if the variability between the actual and predicted heart rates exceeds the baseline variability by a specified threshold.

2. The device of claim 1 wherein the controller is programed to record a patient's intrinsic heart rates and corresponding measured exertion levels as averages.

3. The device of claim 1 wherein the controller is programmed to set an alarm flag if it is determined that a change in chronotropic status has occurred.

4. The device of claim 1 further comprising:
   a telemetry interface for communicating with a remote monitoring device; and,
   wherein the controller is programmed to send an alert message via the telemetry interface if it is determined that a change in chronotropic status has occurred.

5. The device of claim 1 further comprising:
   a pacing channel for pacing a cardiac chamber, wherein the controller is programmed to control the delivery of pacing pulses in accordance with a programmed mode; and,
   wherein the controller is programmed to switch to a rate-adaptive pacing mode if it is determined that a change in chronotropic status has occurred and the patient's actual heart rates are below the predicted heart rates by a specified amount.

6. The device of claim 5 wherein the controller is further programmed to calculate a response factor for rate-adaptive pacing based upon previously measured heart rates and exertion levels.

7. The device of claim 1 wherein the exertion level sensor is a minute ventilation sensor.

8. The device of claim 1 wherein the exertion level sensor is an accelerometer.

9. A method for operating a cardiac rhythm management device, comprising:
   generating intra-cardiac electrogram signals and;
   detecting intrinsic cardiac activity and measuring an intrinsic heart rate from the electrogram signals;
   measuring an exertion level of a patient by measuring a physiological parameter related to metabolic demand;

recording a plurality of a patient's actual intrinsic heart rates along with corresponding measured exertion levels over a period of time;

associating the actual heart rates with predicted heart rates for the corresponding measured exertion levels as calculated in accordance with a physiological model;

calculating a parameter reflecting the variability between the actual heart rates and the predicted heart rates;

comparing the variability between the actual and predicted heart rates with a precomputed baseline variability; and, determining that a change in chronotropic status has occurred if the variability between the actual and predicted heart rates exceeds the baseline variability by a specified threshold.

10. The method of claim 9 further comprising recording a patient's intrinsic heart rates and corresponding measured exertion levels as averages.

11. The method of claim 9 further comprising setting an alarm flag if it is determined that a change in chronotronic status has occurred.

12. The method of claim 9 further comprising:

communicating with a remote monitoring device; and, sending an alert message via the telemetry interface if it is determined that a change in chronotropic status has occurred.

13. The method of claim 9 further comprising:

pacing a cardiac chamber in accordance with a programmed mode; and, switching to a rate-adaptive pacing mode if it is determined that a change in chronotropic status has occurred and the patient's actual heart rates are below the predicted heart rates by a specified amount.

14. The method of claim 13 further comprising calculating a response factor for rate-adaptive pacing based upon previously measured heart rates and exertion levels.

15. The method of claim 9 wherein the exertion level is measured with a minute ventilation sensor.

16. The method of claim 9 wherein the exertion level is measured with an accelerometer.

* * * * *

UNITED STATES PATENT AND TRADEMARK OFFICE
CERTIFICATE OF CORRECTION

PATENT NO.        : 7,142,920 B2  
APPLICATION NO.   : 10/853574  
DATED             : November 28, 2006  
INVENTOR(S)       : Scheiner et al.

It is certified that error appears in the above-identified patent and that said Letters Patent is hereby corrected as shown below:

On the title page, in Item (56), under "U.S. Patent Documents", in column 2, line 10, after "6,572,557" delete "B1" and insert -- B2 --, therefor.

On the title page, in Item (56), under "U.S. Patent Documents", in column 2, line 11, after "6,795,734" delete "B1" and insert -- B2 --, therefor.

In column 6, lines 30–31, in Claim 2, delete "programed" and insert -- programmed --, therefor.

In column 7, line 20, in Claim 11, delete "chronotronic" and insert -- chronotropic --, therefor.

Signed and Sealed this

First Day of May, 2007

JON W. DUDAS  
*Director of the United States Patent and Trademark Office*